US008323663B2

(12) United States Patent
Brough et al.

(10) Patent No.: US 8,323,663 B2
(45) Date of Patent: Dec. 4, 2012

(54) ADENOVIRAL VECTOR-BASED FOOT-AND-MOUTH DISEASE VACCINE

(75) Inventors: Douglas E. Brough, Gaithersburg, MD (US); Joseph T. Bruder, Ijamsville, MD (US); C. Richter King, New York, NY (US); Marvin J. Grubman, Southold, NY (US); John G. Neilan, Wethersfield, CT (US)

(73) Assignee: GenVec, Inc., Gaithersburg, MD (US)

( * ) Notice: Subject to any disclaimer, the term of this patent is extended or adjusted under 35 U.S.C. 154(b) by 63 days.

(21) Appl. No.: 12/117,513

(22) Filed: May 8, 2008

(65) Prior Publication Data

US 2009/0264509 A1 Oct. 22, 2009

Related U.S. Application Data

(63) Continuation of application No. PCT/US2006/060830, filed on Nov. 13, 2206.

(60) Provisional application No. 60/735,439, filed on Nov. 10, 2005.

(51) Int. Cl.
*A61K 39/23* (2006.01)
*A61K 39/285* (2006.01)

(52) U.S. Cl. ............... 424/233.1; 424/202.1; 424/216.1; 424/204.1; 424/184.1

(58) Field of Classification Search ........................ None
See application file for complete search history.

(56) References Cited

U.S. PATENT DOCUMENTS

| | | | |
|---|---|---|---|
| 4,863,457 | A | 9/1989 | Lee |
| 5,168,062 | A | 12/1992 | Stinski |
| 5,378,475 | A | 1/1995 | Smith et al. |
| 5,385,839 | A | 1/1995 | Stinski |
| 5,443,505 | A | 8/1995 | Wong et al. |
| 5,543,328 | A | 8/1996 | McClelland et al. |
| 5,559,099 | A | 9/1996 | Wickham et al. |
| 5,712,136 | A | 1/1998 | Wickham et al. |
| 5,731,190 | A | 3/1998 | Wickham et al. |
| 5,756,086 | A | 5/1998 | McClelland et al. |
| 5,770,442 | A | 6/1998 | Wickham et al. |
| 5,801,030 | A | 9/1998 | McVey et al. |
| 5,824,316 | A | 10/1998 | Grubman et al. |
| 5,837,511 | A | 11/1998 | Falck-Pedersen et al. |
| 5,846,782 | A | 12/1998 | Wickham et al. |
| 5,849,561 | A | 12/1998 | Falck-Pedersen |
| 5,851,806 | A | 12/1998 | Kovesdi et al. |
| 5,871,727 | A | 2/1999 | Curiel |
| 5,885,808 | A | 3/1999 | Spooner et al. |
| 5,922,315 | A | 7/1999 | Roy |
| 5,962,311 | A | 10/1999 | Wickham et al. |
| 5,965,358 | A | 10/1999 | Carrion et al. |
| 5,965,541 | A | 10/1999 | Wickham et al. |
| 5,994,106 | A | 11/1999 | Kovesdi et al. |
| 5,994,128 | A | 11/1999 | Fallaux et al. |
| 5,998,205 | A | 12/1999 | Hallenbeck et al. |
| 6,033,908 | A | 3/2000 | Bout et al. |
| 6,057,155 | A | 5/2000 | Wickham et al. |
| 6,127,175 | A | 10/2000 | Vigne et al. |
| 6,127,525 | A | 10/2000 | Crystal et al. |
| 6,153,435 | A | 11/2000 | Crystal et al. |
| 6,168,941 | B1 | 1/2001 | Liu et al. |
| 6,225,113 | B1 | 5/2001 | Brough et al. |
| 6,225,289 | B1 | 5/2001 | Kovesdi et al. |
| 6,329,190 | B1 | 12/2001 | Wickham et al. |
| 6,329,200 | B1 | 12/2001 | McVey et al. |
| 6,383,795 | B1 | 5/2002 | Carrion et al. |
| 6,440,728 | B1 | 8/2002 | McVey et al. |
| 6,447,995 | B1 | 9/2002 | Carrion et al. |
| 6,455,314 | B1 | 9/2002 | Wickham et al. |
| 6,465,253 | B1 | 10/2002 | Wickham et al. |
| 6,475,757 | B2 | 11/2002 | McVey et al. |
| 6,482,616 | B1 | 11/2002 | Kovesdi et al. |
| 6,514,943 | B2 | 2/2003 | Kovesdi et al. |
| 6,576,456 | B2 | 6/2003 | Wickham et al. |
| 6,586,226 | B2 | 7/2003 | Carrion et al. |
| 6,596,270 | B2 | 7/2003 | Bruder et al. |
| 6,649,373 | B2 | 11/2003 | Brough et al. |
| 6,649,407 | B2 | 11/2003 | Wickham et al. |
| 6,660,521 | B2 | 12/2003 | Brough et al. |
| 6,677,156 | B2 | 1/2004 | Brough et al. |
| 6,682,929 | B2 | 1/2004 | Brough et al. |

(Continued)

FOREIGN PATENT DOCUMENTS

EP 0 105 481 A1 4/1984

(Continued)

OTHER PUBLICATIONS

Catalucci et al., An Adenovirus Type 5 (Ad5) Amplicon-Based Packaging Cell Line for Production of High-Capacity Helper-Independent_E1-E2-E3-E4 Ad5 Vectors, 2007, Journal of Virology, vol. 79, No. 10, pp. 6400-6409.* Fechner et al. Research Article A novel tetracycline-controlled transactivator—transrepressor system enables external control of oncolytic adenovirus replication, 2003, Gene Therapy, vol. 10, pp. 1680-1690.*
Furger et al., Promoter proximal splice sites enhance transcription, 2002, Genes and Development, vol. 16, pp. 2792-2799.*
Adey et al., *Gene*, 156, 27-31 (1995).
Bachrach et al., *J. Immunol.*, 115 (6), 1636-1641 (Dec. 1975).
Bachrach et al., *Intervirology*, 12, 65-72 (1979).
Balass et al., *Analytical Biochem.*, 243, 264-269 (1996).
Brough et al., *Virology*, 196, 269-281 (1993).
Brough et al., *J. Virol.*, 70 (9), 6497-6501 (Sep. 1996).
Brough et al., *J. Virol.*, 71 (12), 9206-9213 (1997).
Buonaguro et al., *ASHI Quarterly*, 3rd Quarter, 78-80 (2005).
Cheng et al., *Gene*, 171, 1-8 (1996).
Chinsangaram et al., *J. Virol.*, 73 (12), 9891-9898 (Dec. 1999).
Cooper et al., *Intervirology*, 10, 165-180 (1978).
Crawford-Miksza et al., *J. Virol.*, 70 (3), 1836-1844 (Mar. 1996).
Einfeld et al., *J. Virol.*, 75 (23), 11284-11291 (Dec. 2001).

(Continued)

*Primary Examiner* — Benjamin P Blumel
(74) *Attorney, Agent, or Firm* — Leydig, Voit & Mayer, Ltd.

(57) ABSTRACT

The invention is directed to an adenoviral vector comprising at least one nucleic acid sequence encoding an *aphthovirus* antigen and/or a cytokine operably linked to a promoter. The adenoviral vector is replication-deficient and requires at most complementation of both the E1 region and the E4 region of the adenoviral genome for propagation. The invention also is directed to a method of inducing an immune response in a mammal comprising administering to the mammal a composition comprising the aforementioned adenoviral vector.

9 Claims, 4 Drawing Sheets

U.S. PATENT DOCUMENTS

| | | | | |
|---|---|---|---|---|
| 6,740,525 | B2 | 5/2004 | Roelvink et al. | |
| 6,908,762 | B2 | 6/2005 | Kovesdi et al. | |
| 6,913,927 | B2 | 7/2005 | Brough et al. | |
| 6,951,755 | B2 | 10/2005 | Wickham et al. | |
| 2001/0043922 | A1 | 11/2001 | Kovesdi et al. | |
| 2002/0004040 | A1 | 1/2002 | Kovesdi et al. | |
| 2002/0031831 | A1 | 3/2002 | Kovesdi et al. | |
| 2002/0110545 | A1 | 8/2002 | Kovesdi et al. | |
| 2003/0099619 | A1 | 5/2003 | Wickham et al. | |
| 2003/0153065 | A1 | 8/2003 | Kovesdi et al. | |
| 2003/0166286 | A1 | 9/2003 | Wickham et al. | |
| 2003/0171314 | A1 | 9/2003 | Grubman et al. | |
| 2004/0161848 | A1 | 8/2004 | Kovesdi | |
| 2005/0233457 | A1 * | 10/2005 | Block | 435/456 |

FOREIGN PATENT DOCUMENTS

| | | | |
|---|---|---|---|
| WO | WO 94/28152 | A1 | 12/1994 |
| WO | WO 95/02697 | A1 | 1/1995 |
| WO | WO 95/16772 | A1 | 6/1995 |
| WO | WO 95/34671 | A1 | 12/1995 |
| WO | WO 96/07734 | A2 | 3/1996 |
| WO | WO 96/22378 | A1 | 7/1996 |
| WO | WO 96/26281 | A1 | 8/1996 |
| WO | WO 97/00326 | A1 | 1/1997 |
| WO | WO 97/12986 | A2 | 4/1997 |
| WO | WO 97/20051 | A2 | 6/1997 |
| WO | WO 97/21826 | A2 | 6/1997 |
| WO | WO 98/07865 | A1 | 2/1998 |
| WO | WO 98/07877 | A1 | 2/1998 |
| WO | WO 98/40509 | A1 | 9/1998 |
| WO | WO 98/53087 | A1 | 11/1998 |
| WO | WO 98/54346 | A1 | 12/1998 |
| WO | WO 98/56937 | A2 | 12/1998 |
| WO | WO 99/15686 | A1 | 4/1999 |
| WO | WO 99/54441 | A1 | 10/1999 |
| WO | WO 00/00628 | A1 | 1/2000 |
| WO | WO 00/12765 | A1 | 3/2000 |
| WO | WO 00/15823 | A1 | 3/2000 |
| WO | WO 00/34444 | A2 | 6/2000 |
| WO | WO 00/34496 | A2 | 6/2000 |
| WO | WO 01/58940 | A2 | 8/2001 |
| WO | WO 01/77304 | A1 | 10/2001 |
| WO | WO 01/92549 | A2 | 12/2001 |
| WO | WO 02/29388 | A2 | 4/2002 |
| WO | WO 02/087336 | A1 | 11/2002 |
| WO | WO 03/020879 | A2 | 3/2003 |
| WO | WO 03/022311 | A1 | 3/2003 |

OTHER PUBLICATIONS

Gheysen et al., *Cell*, 59, 103-112 (Oct. 6, 1989).
Giebel et al, *Biochemistry*, 34, 15430-15435 (1995).
Gorziglia et al., *J. Virol.*, 73 (7), 6048-6055 (Jul. 1999).
Graham et al., *J. Gen. Virol.*, 36, 59-72 (1977).
Houghton et al., *Curr. Opn. Immunol.*, 13, 134-140 (2001).
Katz, Bradley A., *Biochemistry*, 34, 15421-15429 (1995).
Knowles et al., *Veterinary Record*, 148, 258-259 (Mar. 3, 2001).
Krook et al., *Biochem. Biophys. Res. Comm.*, 204 (2), 849-854 (1994).
Laporte et al., *C.R. Acad. Sc. Paris*, 276, 3399-3401 (1973).
Lusky et al., *J. Virol.*, 72 (3), 2022-2032 (Mar. 1998).
Mahy, B.W.J., *Curr. Topics Microbiol. Immunol.*, 288, 1-8, (2005).
Marinovic et al., *J. Biol. Chem.*, 277 (19), 16673-16681 (May 10, 2002).
Mayr et al., *Virology*, 263, 496-506 (1999).
Mayr et al., *Vaccine*, 19, 2152-2162 (2001).
Miyanohara et al., *J. Virol.*, 59 (1), 176-180 (Jul. 1986).
Moraes et al., *Vaccine*, 20, 1631-1639 (2002).
Morita et al., *Gene Ther.*, 8, 1729-1737 (2001).
Morón et al., *J. Immunol.*, 171, 2242-2250 (2003).
Musser et al., *J. Am. Vet .Med. Assoc.*, 224 (8), 1261-1268 (Apr. 15, 2004).
Pacheco et al., *Virology*, 337, 205-209 (2005).
Pasqualini et al., *J. Cell Biol.*, 130 (5), 1189-1196 (Sep. 1995).
Roelvink et al., *Science*, 286, 1568-1571 (Nov. 19, 1999).
Saggio et al., *Biochem. J.*, 293, 613-616 (1993).
Sanz-Parra et al., *J. Gen. Virol.*, 80, 671-679 (1999).
Strohmaier et al., *Biochem. Biophys. Res. Comm.*, 85 (4), 1640-1645 (Dec. 29, 1978).
Van Beusechem et al., *J. Virol.*, 76 (6), 2753-2762 (Mar. 2002).
Van Den Eynde et al., *Curr. Opn. Immunol.*, 9, 684-693 (1997).
Van Der Bruggen et al., *Immunol. Rev.*, 188, 51-64 (2002).
Wagner et al., *Proc. Natl. Acad. Sci. USA*, 78 (3), 1441-1445 (Mar. 1981).
Wickham et al., *Nat. Biotech.*, 14, 1570-1573 (Nov. 1996).
Wild et al., *J. Gen. Virol.*, 1, 247-250 (1967).
Wilson et al., *Nat. Med.*, 1 (9), 887-889 (Sep. 1995).
Worgall et al., *Hum. Gene Ther.*, 8, 37-44 (Jan. 1, 1997).
Wu et al., *Virus Res.*, 93 (2), 211-219 (Jun. 2003).
Brown et al., *J. Virol.*, 70 (8), 5638-5641 (Aug. 1996).
Chinsangaram et al., *J. Virol.*, 72 (5), 4454-4457 (May 1998).
Chinsangaram et al., *Vaccine*, 16 (16), 1516-1522 (1998).
Chinsangaram et al., *J. Virol.*, 75 (12), 5498-5503 (Jun. 2001).
Chinsangaram et al., *J. Virol.*, 77 (2), 1621-1625 (Jan. 2003).
Mason et al., *Virology*, 227, 96-102 (1997).
Mason et al., *Virus Res.*, 91, 9-32 (2003).
Mason et al., *Dev. Biol.*, 114, 79-88 (2003).
Moraes et al., *BioTechniques*, 31, 1050-1056 (Nov. 2001).
Moraes et al., *Vaccine*, 22, 268-279 (2003).
Piccone et al., *J. Virol.*, 69 (8), 4950-4956 (Aug. 1995).
Piccone et al., *J. Virol.*, 69 (9), 5376-5382 (Sep. 1995).
Piccone et al., *Virology*, 226, 135-139 (1996).

* cited by examiner

FIG. 1A

Group A (5x10e9 FFU)

| Cow # | VNT 7 dpv | Days post challenge | | | | | GI | VI |
|---|---|---|---|---|---|---|---|---|
| | | 1 | 2 | 3 | 4 | 5 | | |
| 876 | 1.80 | F | | | | | N | N |
| 877 | 1.20 | F | | | | | N | N |
| 878 | 2.10 | | | | | | N | N |
| 890 | 1.80 | | | | F | | N | N |
| 891 | 1.20 | F | | | | | N | N |
| 896 | 1.50 | F | | | | | N | N |
| 897 | 1.50 | F | | | | | N | N |

FIG. 1B

Group B (1x10e8 FFU)

| Cow # | VNT 7 dpv | Days post challenge | | | | | GI | VI |
|---|---|---|---|---|---|---|---|---|
| | | 1 | 2 | 3 | 4 | 5 | | |
| 524 | 1.80 | F | | | | | N | N |
| 881 | 0.60 | F | F | | | | 2 | N |
| 883 | 1.80 | F | | | F | | N | N |
| 884 | 0.60 | F | | F | | | 2 | P |
| 898 | 1.80 | F | | F | | | N | N |
| 899 | 0.60 | F | | | | | N | N |
| 900 | 0.60 | F | F | | | | 1 | P |

FIG. 1C

Group C (5x10e6 FFU)

| Cow # | VNT 7 dpv | Days post challenge 1 | 2 | 3 | 4 | 5 | GI | VI |
|---|---|---|---|---|---|---|---|---|
| **879** | 0.60 | F | | F | | | **3** | N |
| **880** | 0.60 | F | | F | | | **1** | N |
| **885** | 0.60 | F | F | F | | | N | **P** |
| **886** | 0.60 | F | | | | | **4** | **P** |
| **888** | 0.60 | | F | | | | **4** | **P** |
| **889** | 0.60 | F | F | | | | **1** | **P** |
| **893** | 0.60 | F | F | | | | **1** | **P** |

FIG. 1D

Group D (Control)

| Cow # | VNT 7 d | Days post challenge 1 | 2 | 3 | 4 | 5 | GI | VI |
|---|---|---|---|---|---|---|---|---|
| **525** | 0.60 | F | F | F | F | | **3** | N |
| **882** | 0.60 | F | | | | | **1** | N |
| **887** | 0.60 | F | F | | | | N | **P** |
| **892** | 0.60 | | | | | | **4** | **P** |
| **894** | 0.60 | | F | F | F | | **4** | **P** |
| **895** | 0.60 | F | | | | | **1** | **P** |

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Cys Arg Gly Asp Cys
1               5


<210> SEQ ID NO 2
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: "X" may be any amino acid
<220> FEATURE:
<221> NAME/KEY: MISC_FEATURE
<222> LOCATION: (8)..(8)
<223> OTHER INFORMATION: "X" may be any amino acid

<400> SEQUENCE: 2

Cys Xaa Cys Arg Gly Asp Cys Xaa Cys
1               5


<210> SEQ ID NO 3
<211> LENGTH: 9
<212> TYPE: PRT
<213> ORGANISM: Artificial
<220> FEATURE:
<223> OTHER INFORMATION: Synthetic
```

-continued

```
<400> SEQUENCE: 3

Cys Asp Cys Arg Gly Asp Cys Phe Cys
1               5


<210> SEQ ID NO 4
<211> LENGTH: 58
<212> TYPE: DNA
<213> ORGANISM: Escherichia coli

<400> SEQUENCE: 4

agctctccct atcagtgata gagatctccc tatcagtgat agagatcgtc gacgagct        58
```

ADENOVIRAL VECTOR-BASED FOOT-AND-MOUTH DISEASE VACCINE

CROSS-REFERENCE TO RELATED APPLICATIONS

This patent application is a continuation of copending International Patent Application No. PCT/US2006/060830, filed Nov. 13, 2006, designating the United States, which claims the benefit of U.S. Provisional Patent Application No. 60/735,439, filed Nov. 10, 2005.

STATEMENT REGARDING FEDERALLY SPONSORED RESEARCH AND DEVELOPMENT

This invention was made with Government support under Other Transaction Agreement (OTA) No. HSHQDC-07-9-00004 awarded by the United States Department of Homeland Security (DHS). The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,139 Byte ASCII (Text) file named "702949_ST25.TXT," created on Jun. 23, 2009.

BACKGROUND OF THE INVENTION

Foot-and-mouth disease (FMD) is a highly contagious disease of cloven-hooved animals, including cattle, swine, sheep, goats, and deer, that rapidly replicates in the host and spreads to susceptible animals by contact or aerosol. Because of the highly infectious nature of FMD, countries free of the disease maintain rigid quarantine and import restrictions on animals and animal products from infected countries in order to prevent its introduction and to allow continued active participation in international trade. The disease does not occur in the U.S., Canada, or Mexico, and its continued absence from North America is a priority for the U.S. livestock industry and the United States Department of Agriculture (USDA).

The virus that causes FMD (FMDV) is an RNA virus classified as a member of the genus *Aphthovirus* and the family Picornaviridae (see Cooper et al., *Intervirology,* 10: 165-180 (1978)). There are seven known serotypes of FMDV: the European serotypes A, O and C, the South Africa Territories serotypes SAT 1, SAT 2, and SAT 3, and the Asia 1 serotype. A number of antigenically distinct subtypes are recognized within each of these serotypes. Indeed, for each serotype or subtype several genetically distinct variants exist.

Disease incidence in previously FMD-free countries, such as the United Kingdom in 2001 (see, e.g. Knowles et al., *Vet. Rec.,* 148: 258-259 (2001)) are controlled by inhibition of susceptible animal movement, slaughter of infected and in-contact animals, and decontamination. Inactivated whole virus vaccines are conventionally used in FMD control programs as a last resort mainly because of the adverse economic affects of vaccination as compared to slaughter, despite their success in controlling the disease. Other problems associated with the currently available FMD vaccine include a requirement for high-containment facilities to produce the virus needed for vaccine manufacture, the antigenic variation of the virus resulting in numerous virus serotypes and subtypes, and the inability of vaccines to rapidly induce protective immunity.

To circumvent these problems, researchers have explored using viral vectors as FMD vaccines. For example, E1-deficient adenoviral vectors have been engineered to encode the FMD virus (FMDV) empty capsid and the 3C protease (Pacheco et al., *Virology,* 337: 205-209 (2005)), as well as interferons (U.S. Patent Application Publication 2003/0171314 A1). Such adenoviral vectors, however, have not been shown to induce the rapid antibody response required to combat an FMDV outbreak.

Accordingly, there remains a need for viral vector vaccines that elicit a more rapid and complete immune response against foot-and-mouth disease. The invention provides such viral vectors.

BRIEF SUMMARY OF THE INVENTION

The invention provides an adenoviral vector comprising an adenoviral genome and at least one nucleic acid sequence encoding an *aphthovirus* antigen and/or a cytokine operably linked to a promoter, wherein the adenoviral vector is replication-deficient and requires complementation of both the E1 region and the E4 region of the adenoviral genome for propagation.

BRIEF DESCRIPTION OF THE SEVERAL VIEWS OF THE DRAWING(S)

FIG. 1A is a table illustrating the results of a vaccination-challenge study in cattle immunized with $5\times10^9$ FFU of the adenoviral vector A24 GV11. "VNT" denotes virus neutralization titer, "VI" denotes virus isolation, "GI" denotes generalization of infection, "F" denotes fever, "N" denotes negative, and "P" denotes positive.

FIG. 1B is a table illustrating the results of a vaccination-challenge study in cattle immunized with $1\times10^8$ FFU of the adenoviral vector A24 GV11. "VNT" denotes virus neutralization titer, "VI" denotes virus isolation, "GI" denotes generalization of infection, "F" denotes fever, "N" denotes negative, and "P" denotes positive.

FIG. 1C is a table illustrating the results of a vaccination-challenge study in cattle immunized with $5\times10^6$ FFU of the adenoviral vector A24 GV11. "VNT" denotes virus neutralization titer, "VI" denotes virus isolation, "GI" denotes generalization of infection, "F" denotes fever, "N" denotes negative, and "P" denotes positive.

FIG. 1D is a table illustrating the results of a vaccination-challenge study in control cattle that were not immunized prior to FMDV challenge. "VNT" denotes virus neutralization titer, "VI" denotes virus isolation, "GI" denotes generalization of infection, "F" denotes fever, "N" denotes negative, and "P" denotes positive.

DETAILED DESCRIPTION OF THE INVENTION

Figure 2A:
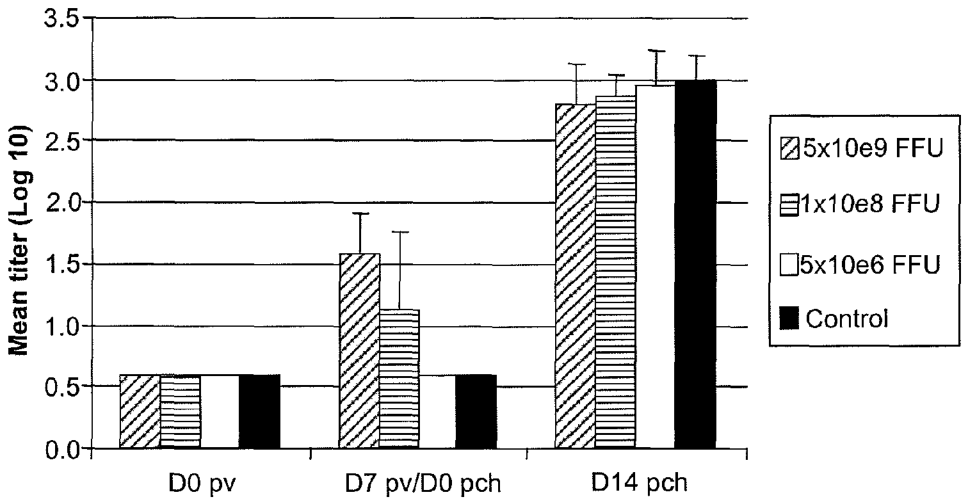
FIG. 2A is a graph illustrating the neutralizing antibody response against FMDV strain A24 in cattle produced as a result of the vaccination-challenge study described in Example 1. The antibody titers were measured prior to vaccination (D0pv), seven days after vaccination (D7 pv/D0 pch), and 14 days post challenge (D14 pch).

The invention provides an adenoviral vector comprising an adenoviral genome comprising at least one nucleic acid sequence encoding an *aphthovirus* antigen and/or a cytokine operably linked to a promoter, wherein the adenoviral vector is replication-deficient and requires at most complementation of both the E1 region and the E4 region of the adenoviral genome for propagation. Adenovirus (Ad) is a 36 kb double-stranded DNA virus that efficiently transfers DNA in vivo to a variety of different target cell types. For use in the invention, the adenovirus is preferably made replication deficient by deleting, in whole or in part, select genes required for viral replication. The expendable E3 region is also frequently deleted, in whole or in part, to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors can be a desirable option for use in the invention.

Adenovirus from various origins, subtypes, or mixture of subtypes can be used as the source of the viral genome for the adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561 and International Patent Applications WO 97/12986 and WO 98/53087.

The adenoviral vector can comprise a mixture of subtypes and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise different or approximately equal amounts of the genome of each of the two or more different adenovirus serotypes. When the chimeric adenoviral vector genome is comprised of the genomes of two different adenovirus serotypes, the chimeric adenoviral vector genome preferably comprises no more than about 70% (e.g., no more than about 65%, about 50%, or about 40%) of the genome of one of the adenovirus serotypes, with the remainder of the chimeric adenovirus genome being derived from the genome of the other adenovirus serotype. In one embodiment, the chimeric adenoviral vector can contain an adenoviral genome comprising a portion of a serotype 2 genome and a portion of a serotype 5 genome. For example, nucleotides 1-456 of such an adenoviral vector can be derived from a serotype 2 genome, while the remainder of the adenoviral genome can be derived from a serotype 5 genome.

The adenoviral vector of the invention can be replication-competent. For example, the adenoviral vector can have a mutation (e.g., a deletion, an insertion, or a substitution) in the adenoviral genome that does not inhibit viral replication in host cells. The adenoviral vector also can be conditionally replication-competent. Preferably, however, the adenoviral vector is replication-deficient in host cells.

By "replication-deficient" is meant that the adenoviral vector requires complementation of one or more regions of the adenoviral genome that are required for replication, as a result of, for example, a deficiency in at least one replication-essential gene function (i.e., such that the adenoviral vector does not replicate in typical host cells, especially those in an animal that could be infected by the adenoviral vector in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The replication-deficient adenoviral vector desirably requires complementation of at least one replication-essential gene function of one or more regions of the adenoviral genome. Preferably, the adenoviral vector requires complementation of at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application Publication WO 00/00628. Most preferably, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenoviral vector also can require complementation of the E4 region of the adenoviral genome for replication, such as through a deficiency in one or more replication-essential gene functions of the E4 region.

When the adenoviral vector is E1-deficient, the adenoviral vector genome can comprise a deletion beginning at any nucleotide between nucleotides 335 to 375 (e.g., nucleotide 356) and ending at any nucleotide between nucleotides 3,310 to 3,350 (e.g., nucleotide 3,329) or even ending at any nucleotide between 3,490 and 3,530 (e.g., nucleotide 3,510) (based on the adenovirus serotype 5 genome). When E2A-deficient, the adenoviral vector genome can comprise a deletion beginning at any nucleotide between nucleotides 22,425 to 22,465 (e.g., nucleotide 22,443) and ending at any nucleotide between nucleotides 24,010 to 24,050 (e.g., nucleotide 24,032) (based on the adenovirus serotype 5 genome). When E3-deficient, the adenoviral vector genome can comprise a deletion beginning at any nucleotide between nucleotides 28,575 to 29,615 (e.g., nucleotide 28,593) and ending at any nucleotide between nucleotides 30,450 to 30,490 (e.g., nucleotide 30,470) (based on the adenovirus serotype 5 genome). When E4-deficient, the adenoviral vector genome can comprise a deletion beginning at, for example, any nucleotide between nucleotides 32,805 to 32,845 (e.g., nucleotide 32,826) and ending at, for example, any nucleotide between nucleotides 35,540 to 35,580 (e.g., nucleotide 35,561) (based on the adenovirus serotype 5 genome). The endpoints defining the deleted nucleotide portions can be difficult to precisely determine and typically will not significantly affect the nature of the adenoviral vector, i.e., each of the aforementioned nucleotide numbers can be ±1, 2, 3, 4, 5, or even 10 or 20 nucleotides.

When the adenoviral vector is deficient in at least one replication-essential gene function in one region of the adenoviral genome (e.g., an E1- or E1/E3-deficient adenoviral vector), the adenoviral vector is referred to as "singly replication-deficient." A particularly preferred singly replication-deficient adenoviral vector is, for example, a replication-deficient adenoviral vector requiring, at most, complementation of the E1 region of the adenoviral genome, so as to propagate the adenoviral vector (e.g., to form adenoviral vector particles).

The adenoviral vector can be "multiply replication-deficient," meaning that the adenoviral vector is deficient in one or more replication-essential gene functions in each of two or more regions of the adenoviral genome, and requires complementation of those functions for replication. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). When the adenoviral vector is multiply replication-deficient, the deficiencies can be a combination of the nucleotide deletions discussed above with respect to each individual region. An adenoviral vector deleted of the entire E4 region can elicit a lower host immune response.

If the adenoviral vector of the invention is deficient in a replication-essential gene function of the E2A region, the vector preferably does not comprise a complete deletion of the E2A region, which deletion preferably is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology,* 196: 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that any multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5. This portion of the adenoviral genome desirably is included in the adenoviral vector because it is not complemented in current E2A cell lines so as to provide the desired level of viral propagation.

While the above-described deletions are described with respect to an adenovirus serotype 5 genome, one of ordinary skill in the art can determine the nucleotide coordinates of the same regions of other adenovirus serotypes, such as an adenovirus serotype 2 genome, without undue experimentation, based on the similarity between the genomes of various adenovirus serotypes, particularly adenovirus serotypes 2 and 5.

In one embodiment of the invention, the adenoviral vector can comprise an adenoviral genome deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. Most preferably, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

It should be appreciated that the deletion of different regions of the adenoviral vector can alter the immune response of the mammal. In particular, deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent disorders.

The adenoviral vector, when multiply replication-deficient, especially in replication-essential gene functions of the E1 and E4 regions, can include a spacer sequence to provide viral growth in a complementing cell line similar to that achieved by singly replication-deficient adenoviral vectors, particularly an E1-deficient adenoviral vector. In a preferred E4-deficient adenoviral vector of the invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication-deficient adenoviral vector, particularly a singly replication-deficient E1 deficient adenoviral vector.

The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer sequence can be coding or non-coding and native or non-native with respect to the adenoviral genome, but does not restore the replication-essential function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promoter is not present in the vector, the spacer is proximal to the right-side ITR. The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. Ideally, the spacer is composed of the glucuronidase gene. The use of a spacer in an adenoviral vector is further described in, for example, U.S. Pat. No. 5,851,806 and International Patent Application WO 97/21826.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. Nos. 6,225,113, 6,649,373, and 6,660,521, and International Patent Application Publication WO 00/34496. In view of the above, a replication-deficient adenoviral vector (e.g., the at least E4-deficient adenoviral vector) or a second expression vector can comprise a nucleic acid sequence encoding a trans-acting factor that modulates the persistence of expression of the nucleic acid sequence. Persistent expression of antigenic DNA can be desired when generating immune tolerance.

Desirably, the adenoviral vector requires, at most, complementation of replication-essential gene functions of the E1, E2A, and/or E4 regions of the adenoviral genome for replication (i.e., propagation). However, the adenoviral genome can be modified to disrupt one or more replication-essential gene functions as desired by the practitioner, so long as the adenoviral vector remains deficient and can be propagated using, for example, complementing cells and/or exogenous DNA (e.g., helper adenovirus) encoding the disrupted replication-essential gene functions. In this respect, the adenoviral vector can be deficient in replication-essential gene functions of only the early regions of the adenoviral genome, only the late regions of the adenoviral genome, and both the early and late regions of the adenoviral genome. Suitable replication-deficient adenoviral vectors, including singly and multiply replication-deficient adenoviral vectors, are disclosed in U.S. Pat. Nos. 5,837,511, 5,851,806, 5,994,106, 6,127,175, and 6,482,616; U.S. Patent Application Publications 2001/0043922 A1, 2002/0004040 A1, 2002/0031831 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

By removing all or part of, for example, the E1, E3, and E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector.

Replication-deficient adenoviral vectors are typically produced in complementing cell lines that provide gene functions not present in the replication-deficient adenoviral vectors, but required for viral propagation, at appropriate levels in order to generate high titers of viral vector stock. Desirably, the complementing cell line comprises, integrated into the cellular genome, adenoviral nucleic acid sequences which encode gene functions required for adenoviral propagation. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially vaccination purposes. The lack of RCA in the vector stock avoids the replication of the adenoviral vector in non-complementing cells. Construction of such a complementing cell lines involve standard molecular biology and cell culture techniques, such as those described by Sambrook et al., *Molecular Cloning, a Laboratory Manual,* 3*rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

Complementing cell lines for producing the adenoviral vector include, but are not limited to, 293 cells (described in, e.g., Graham et al., *J. Gen. Virol.,* 36: 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

If the adenoviral vector is not replication-deficient, ideally the adenoviral vector is manipulated to limit replication of the vector to within a target tissue. The adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. In autoimmune disease treatment, it can be advantageous to control adenoviral vector replication in, for instance, lymph nodes, to obtain continual antigen production and control immune cell production. Conditionally-replicating adenoviral vectors are described further in U.S. Pat. No. 5,998,205.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate expression vector construction. For example, it can be advantageous to remove or introduce restriction enzyme sites in the adenoviral genome. Such benign mutations often have no detectable adverse effect on viral functioning. For example, the adenoviral vector can comprise a deletion of nucleotides 10,594 and 10,595 (based on the adenoviral serotype 5 genome), which are associated with VA-RNA-1 transcription, but the deletion of which does not prohibit production of VA-RNA-1.

Similarly, it will be appreciated that numerous adenoviral vectors are available commercially. Construction of adenoviral vectors is well understood in the art. Adenoviral vectors can be constructed and/or purified using methods known in the art (e.g., using complementing cell lines, such as the 293 cell line, PER.C6 cell line, or 293-ORF6 cell line) and methods set forth, for example, in U.S. Pat. Nos. 5,965,358, 5,994,128, 6,033,908, 6,168,941, 6,329,200, 6,383,795, 6,440,728, 6,447,995, 6,475,757, 6,586,226, 6,908,762, and 6,913,927; and International Patent Applications WO 98/53087, WO 98/56937, WO 99/15686, WO 99/54441, WO 00/12765, WO 01/77304, and WO 02/29388, as well as the other references identified herein.

In another embodiment, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by a viral vector or enable targeting of a viral vector to a specific cell type.

Any suitable technique for altering native binding to a host cell, such as native binding of the fiber protein to the coxsackievirus and adenovirus receptor (CAR) of a cell, can be employed. For example, differing fiber lengths can be exploited to ablate native binding to cells. This optionally can be accomplished via the addition of a binding sequence to the penton base or fiber knob. This addition of a binding sequence can be done either directly or indirectly via a bispecific or multispecific binding sequence. In an alternative embodiment, the adenoviral fiber protein can be modified to reduce the number of amino acids in the fiber shaft, thereby creating a "short-shafted" fiber (as described in, for example, U.S. Pat. No. 5,962,311). Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a non-native amino acid sequence either into the penton base or the fiber knob.

In another embodiment, the nucleic acid residues encoding amino acid residues associated with native substrate binding can be changed, supplemented, or deleted (see, e.g., International Patent Application Publication WO 00/15823, Einfeld et al., *J. Virol.,* 75(23): 11284-11291 (2001), and van Beusechem et al., *J. Virol.,* 76(6): 2753-2762 (2002)) such that the adenoviral vector incorporating the mutated nucleic acid residues (or having the fiber protein encoded thereby) is less able to bind its native substrate. In this respect, the native CAR and integrin binding sites of the adenoviral vector, such as the knob domain of the adenoviral fiber protein and an Arg-Gly-Asp (RGD) sequence located in the adenoviral penton base, respectively, can be removed or disrupted. Any suitable amino acid residue(s) of a fiber protein that mediates or assists in the interaction between the knob and CAR can be mutated or removed, so long as the fiber protein is able to trimerize. Similarly, amino acids can be added to the fiber knob as long as the fiber protein retains the ability to trimerize. Suitable residues include amino acids within the exposed loops of the serotype 5 fiber knob domain, such as, for example, the AB loop, the DE loop, the FG loop, and the HI loop, which are further described in, for example, Roelvink et al., *Science,* 286: 1568-1571 (1999), and U.S. Pat. No. 6,455,314. Any suitable amino acid residue(s) of a penton base protein that mediates or assists in the interaction between the penton base and integrins can be mutated or removed. Suitable residues include, for example, one or more of the five RGD amino acid sequence motifs located in the hypervariable region of the Ad5 penton base protein (as described, for example, U.S. Pat. No. 5,731,190). The native integrin binding sites on the penton base protein also can be disrupted by modifying the nucleic acid sequence encoding the native RGD motif such that the native RGD amino acid sequence is conformationally inaccessible for binding to the αv integrin receptor, such as by inserting a DNA sequence into or adjacent to the nucleic acid sequence encoding the adenoviral penton base protein. Preferably, the adenoviral vector comprises a fiber protein and a penton base protein that do not bind to CAR and integrins, respectively. Alternatively, the adenoviral vector comprises fiber protein and a penton base protein that bind to CAR and integrins, respectively, but with less affinity than the corresponding wild type coat proteins. The adenoviral vector exhibits reduced binding to CAR and integrins if a modified adenoviral fiber protein and penton base protein binds CAR and integrins, respectively, with at least about 5-fold, 10-fold, 20-fold, 30-fold, 50-fold, or 100-fold less affinity than a non-modified adenoviral fiber protein and penton base protein of the same serotype.

The adenoviral vector also can comprise a chimeric coat protein comprising a non-native amino acid sequence that binds a substrate (i.e., a ligand), such as a cellular receptor other than CAR the αv integrin receptor. Such a chimeric coat protein allows an adenoviral vector to bind, and desirably, infect host cells not naturally infected by the corresponding adenovirus that retains the ability to bind native cell surface receptors, thereby further expanding the repertoire of cell types infected by the adenoviral vector. The non-native amino acid sequence of the chimeric adenoviral coat protein allows an adenoviral vector comprising the chimeric coat protein to bind and, desirably, infect host cells not naturally infected by a corresponding adenovirus without the non-native amino acid sequence (i.e., host cells not infected by the corresponding wild-type adenovirus), to bind to host cells naturally infected by the corresponding adenovirus with greater affinity than the corresponding adenovirus without the non-native amino acid sequence, or to bind to particular target cells with greater affinity than non-target cells. A "non-native" amino acid sequence can comprise an amino acid sequence not naturally present in the adenoviral coat protein or an amino acid sequence found in the adenoviral coat but located in a non-native position within the capsid. By "preferentially binds" is meant that the non-native amino acid sequence binds a receptor, such as, for instance, αvβ3 integrin, with at least about 3-fold greater affinity (e.g., at least about 5-fold, 10-fold, 15-fold, 20-fold, 25-fold, 35-fold, 45-fold, or 50-fold greater affinity) than the non-native ligand binds a different receptor, such as, for instance, αvβ1 integrin.

Desirably, the adenoviral vector comprises a chimeric coat protein comprising a non-native amino acid sequence that confers to the chimeric coat protein the ability to bind to an immune cell more efficiently than a wild-type adenoviral coat protein. In particular, the adenoviral vector can comprise a chimeric adenoviral fiber protein comprising a non-native amino acid sequence which facilitates uptake of the adenoviral vector by immune cells, preferably antigen presenting cells, such as dendritic cells, monocytes, and macrophages. In a preferred embodiment, the adenoviral vector comprises a chimeric fiber protein comprising an amino acid sequence (e.g., a non-native amino acid sequence) comprising an RGD motif including, but not limited to, CRGDC (SEQ ID NO: 1), CXCRGDCXC (SEQ ID NO: 2), wherein X represents any amino acid, and CDCRGDCFC (SEQ ID NO: 3), which increases transduction efficiency of an adenoviral vector into dendritic cells. The RGD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence. The spacer sequence preferably comprises between one and two-hundred amino acids, and can (but need not) have an intended function.

Where dendritic cells are the desired target cell, the non-native amino acid sequence can optionally recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include αvβ3 integrins, αvβ5 integrins, 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc. Where dendritic cells are targeted, the ligand preferably recognizes the CD40 cell surface protein, such as, for example, by way of a CD-40 (bi)specific antibody fragment or by way of a domain derived from the CD40L polypeptide.

Where macrophages are the desired target, the non-native amino acid sequence optionally can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, heparin sulfate proteoglycans, αvβ3 integrins, αvβ5 integrins, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor b, HLA Class I, Sialoadhesin, siglec-5, and the toll-like receptor-2 (TLR2).

Where B-cells are the desired target, the non-native amino acid sequence can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fcα, Fcγ, Fcε, etc.), IgM, gp200-MR6, Growth Hormone Receptor (GHi-R), ICAM-1, ILT2, CD85, MHC class I and II molecules, transforming growth factor receptor (TGF-R), α4β7 integrin, and αvβ3 integrin.

In another embodiment of the invention, the adenoviral vector comprises a chimeric virus coat protein not selective for a specific type of eukaryotic cell. The chimeric coat protein differs from the wild-type coat protein by an insertion of a non-native amino acid sequence into or in place of an internal coat protein sequence. In this embodiment, the chimeric adenovirus coat protein efficiently binds to a broader range of eukaryotic cells than a wild-type adenovirus coat, such as described in International Patent Application WO 97/20051.

The ability of an adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, proteins IX, VI, or IIIa, etc. The sequences of such proteins, and methods for employing them in recombinant proteins, are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the ligand domain is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to the hexon, preferably it is within a hypervariable region (Crawford-Miksza et al., *J. Virol.,* 70 (3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

Binding affinity of a non-native amino acid sequence to a cellular receptor can be determined by any suitable assay, a variety of which assays are known and are useful in selecting a non-native amino acid sequence for incorporating into an adenoviral coat protein. Desirably, the transduction levels of host cells are utilized in determining relative binding efficiency. Thus, for example, host cells displaying αvβ3 integrin on the cell surface (e.g., MDAMB435 cells) can be exposed to an adenoviral vector comprising the chimeric coat protein and the corresponding adenovirus without the non-native amino acid sequence, and then transduction efficiencies can be compared to determine relative binding affinity. Similarly, both host cells displaying αvβ3 integrin on the cell surface (e.g., MDAMB435 cells) and host cells displaying predominantly αvβ1 on the cell surface (e.g., 293 cells) can be exposed to the adenoviral vectors comprising the chimeric coat protein, and then transduction efficiencies can be compared to determine binding affinity.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol,* 130: 1189 (1995)). A ligand can even bind non-peptide substrates, such as plastic (e.g., Adey et al., *Gene,* 156: 27 (1995)), biotin (Saggio et al., *Biochem. J.,* 293: 613 (1993)), a DNA sequence (Cheng et al., *Gene,* 171: 1 (1996), and Krook et al., *Biochem. Biophys., Res. Commun.,* 204: 849 (1994)), streptavidin (Geibel et al., *Biochemistry,* 34: 15430 (1995), and Katz, *Biochemistry,* 34: 15421 (1995)), nitrostreptavidin (Balass et al., *Anal. Biochem.,* 243: 264 (1996)), heparin (Wickham et al., *Nature Biotechnol.,* 14: 1570-73 (1996)), and other substrates.

Disruption of native binding of adenoviral coat proteins to a cell surface receptor can also render it less able to interact with the innate or acquired host immune system. Aside from pre-existing immunity, adenoviral vector administration induces inflammation and activates both innate and acquired immune mechanisms. Adenoviral vectors activate antigen-specific (e.g., T-cell dependent) immune responses, which limit the duration of transgene expression following an initial administration of the vector. In addition, exposure to adenoviral vectors stimulates production of neutralizing antibodies by B cells, which can preclude gene expression from subsequent doses of adenoviral vector (Wilson and Kay, *Nat. Med.,* 3(9): 887-889 (1995)). Indeed, the effectiveness of repeated administration of the vector can be severely limited by host immunity. In addition to stimulation of humoral immunity, cell-mediated immune functions are responsible for clearance of the virus from the body. Rapid clearance of the virus is attributed to innate immune mechanisms (see, e.g., Worgall et al., *Human Gene Therapy,* 8: 37-44 (1997)), and likely involves Kupffer cells found within the liver. Thus, by ablating native binding of an adenovirus fiber protein and penton base protein, immune system recognition of an adenoviral vector is diminished, thereby increasing vector tolerance by the host.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, 6,576,456, 6,596,270, 6,649,407, 6,740,525; 6,951,755; U.S. Patent Application Publications 2003/0099619 A1, 2003/0166286 A1, and 2004/0161848 A1; and International Patent Applications WO 95/02697, WO 95/16772, WO 95/34671, WO 96/07734, WO 96/22378, WO 96/26281, WO 97/20051, WO 98/07865, WO 98/07877, WO 98/40509, WO 98/54346, WO 00/15823, WO 01/58940, and WO 01/92549.

Any type of nucleic acid sequence (e.g., DNA, RNA, and cDNA) that can be inserted into an adenoviral vector can be used in connection with the invention. Preferably, each nucleic acid sequence is DNA, and preferably encodes a protein (i.e., one or more nucleic acid sequences encoding one or more proteins). In a particularly preferred embodiment, at least one nucleic acid sequence encodes an antigen. An "antigen" is a molecule that induces an immune response in a mammal. An "immune response" can entail, for example, antibody production and/or the activation of immune effector cells (e.g., T cells). An antigen in the context of the invention can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. By "epitope" is meant a sequence on an antigen that is recognized by an antibody or an antigen receptor. Epitopes also are referred to in the art as "antigenic determinants."

In one embodiment, the antigen can be a viral antigen. The viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus), Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B), Papovaviridae, Paramyxoviridae (e.g., measles, mumps, and human respiratory syncytial virus), Parvoviridae, Picornaviridae (e.g., poliovirus, rhinovirus, hepatovirus, and *aphthovirus*), Poxviridae (e.g., vaccinia virus), Reoviridae (e.g., *rotavirus*), Retroviridae (e.g., lentivirus, such as human immunodeficiency virus (HIV) 1 and HIV 2), Rhabdoviridae, and Totiviridae. Particularly preferred retroviridae (retrovirus) antigens include, for example, HIV antigens, such as all or part of the gag, env, or pol proteins, or fusion proteins comprising all or part of the gag, env, or pol proteins. Any clade of HIV is appropriate for antigen selection, including clades A, B, C, MN, and the like. Particularly preferred coronavirus antigens include, for example, SARS virus antigens. Suitable SARS virus antigens for the invention include, for example, all or part of the E protein, the M protein, and the spike protein of the SARS virus. Suitable viral antigens also include all or part of Dengue protein M, Dengue protein E, Dengue D1NS1, Dengue D1NS2, and Dengue D1NS3. The antigenic peptides specifically recited herein are merely exemplary as any viral protein can be used in the context of the invention.

In a preferred embodiment of the invention, the antigen is an *aphthovirus* antigen. Preferably, the antigen is a foot-and-mouth disease virus (FMDV) antigen. There are seven known serotypes of FMDV, and over 60 known subtypes (see, e.g., Mahy, *Curr. Top. Microbiol. Immunol.,* 288: 1-8 (2005), and Musser, *J. Am. Vet. Med. Assoc.,* 224(8): 1261-8 (2004)). FMDV antigens are generally known to those of skill in the art, and include, but are not limited to, antigens of FMDV serotypes A (e.g., subtypes A24 and A12), O (e.g., subtypes O1C and O1M), C, Asia 1, SAT 1, SAT 2, and SAT 3. In a preferred embodiment, the antigen is obtained from strain A24 Cruzeiro, Asia 1, O1C, or O1M. One of ordinary skill in the art will appreciate that each FMDV serotype is antigenically distinct from the other serotypes. Furthermore, within each serotype there is considerable antigenic diversity. Thus, antisera raised against one strain of FMDV serotype may not recognize other strains of the same serotype.

The FMDV particle consists of a single strand of RNA and four polypeptides, namely 1A, 1B, 1C, and 1D, collectively referred to as P1, which form the capsid proteins of the virus. The P1 protein also is referred to in the art as VP 1, VPThr, and VPT (see Bachrach, et al., *J. Immunology,* 115: 1636-1641 (1975)), Strohmaier et al., *Biochem. Biophys. Res. Comm.,* 85: 1640-1645 (1978), and Bachrach et al., *Intervirology,* 12: 65-72 (1979)). It is generally considered that there are approximately 60 copies of each capsid protein in the virus. Capsid protein 1A is susceptible to cleavage when intact virus is treated with trypsin, resulting in a large decrease in infectivity of most strains of FMDV (see e.g., Wild et al., *J. Gen. Virology,* 1: 247-250 (1967)). Trypsin treatment may also reduce the capacity of virus to stimulate the production of neutralizing antibody. Thus, protein 1A likely is the most immunogenic structural FMDV protein, and is capable of eliciting effective protection against infection by FMDV. In this regard, protein 1A separated from virus particles has been shown to produce neutralizing antibodies and elicit effective protection against the virus (see Laporte et al., *C.R. Acad. Sc. Paris,* 276: 3399-5401 (1973), and Bachrach et al., *Immunology,* 115: 1636-1641 (1975)). The antigen also can be derived from a nonstructural protein of FMDV. FMDV nonstructural proteins include the P2 protein (i.e., proteins 2A, 2B, and 2C) and the P3 protein (i.e., proteins 3A, 3B, 3C, and 3D). Antigenic peptides of FMDV are disclosed in, for example, European Patent No. 0105481.

In a preferred embodiment of the invention, the antigen is an empty virus capsid of FMDV. An "empty virus capsid" contains only the portion of the FMDV genome encoding the viral structural proteins and the 3C protein, which is required for capsid formation (see Mayr et al., *Virology,* 263: 496-506 (1999)), and does not contain the infectious viral nucleic acid. Thus, animals inoculated with an empty virus capsid can be distinguished from infected or convalescent animals using approved diagnostic assays (see, e.g., Mayr et al., *Virology,* 263: 496-506 (1999), and Mayr et al., *Vaccine,* 19: 2152-2162 (2001)), as well as with diagnostic assays using the most immunogenic non-structural protein, 3D (see, e.g., Pacheco et al., supra). Vaccination of swine and cattle with an empty viral capsid from FMDV strain A24 Cruzeiro delivered by an E1-deficient adenoviral vector can protect animals when challenged by direct inoculation of the heel bulb with virulent homologous virus (see Moraes et al., *Vaccine,* 20: 1631-1639 (2002), and Pacheco et al., supra).

When the antigen is an empty virus capsid of FMDV, the viral structural proteins and the 3C protein preferably are derived from a virus of the same serotype and subtype. For example, when the antigen is an empty virus capsid of the A24 Cruzeiro FMDV strain, both the virus structural proteins and the 3C protein preferably are also of the A24 Cruzeiro FMDV strain. Similarly, when the antigen is an empty virus capsid of the Asia1 serotype, both the virus structural proteins and the 3C protein preferably are also of the Asia1 serotype. When the antigen is an empty virus capsid of the O1C strain, both the virus structural proteins and the 3C protein are also of the O1C strain. Antigens comprising FMDV empty virus capsids from different FMDV serotypes are also within the scope of the invention. In this respect, an FMDV empty virus capsid can contain one or more virus structural proteins and/or a 3C protein derived from a first FMDV serotype, and one or more virus structural proteins and/or a 3C protein derived from a second FMDV serotype. For example, the antigen can comprise virus structural proteins from the A24 Cruzeiro FMDV strain, while the 3C protein can be from the Asia1 strain. Similarly, the antigen can comprise virus structural proteins from the O1C strain, while the 3C protein can be from the A24 Cruzeiro strain. These specific embodiments, however, are merely exemplary. One of ordinary skill in the art will appreciate that genes from any combination of FMDV serotypes can be utilized to generate the empty virus capsid antigen.

In addition to being an antigen itself, the FMDV empty capsid also can be used in the invention as a virus-like particle (VLP) to deliver an antigen (e.g., a *Plasmodium* antigen, an HIV antigen, or a tumor antigen) to an appropriate host. A "virus-like particle" consists of one or more viral coat proteins that assemble into viral particles, but lacks any viral genetic material (see, e.g., Miyanohara et al., *J. Virol.,* 59: 176-180 (1986), Gheysen et al., *Cell,* 59: 103-112 (1989), and Buonaguro et al., *ASHI Quarterly,* 29: 78-80 (2005)). VLPs can be presented by antigen presenting cells (APCs) on MHC class II molecules, which correlates with activation of CD4+ helper T cells. Recent evidence also indicates that VLPs can be presented on MHC class I molecules, thereby inducing CD8+ cytotoxic T cell activation (see, e.g., Moron et al., *J. Immunol.,* 171: 2242-2250 (2003)). Thus, VLPs can elicit effective B cell and T cell immune responses. In the context of the invention, the adenovirus comprises at least one nucleic acid sequence encoding an FMDV empty capsid, and at least one nucleic acid sequence encoding an antigen, wherein the nucleic acid sequence encoding the FMDV empty capsid is modified so as to display the antigen on its surface. The nucleic acid sequence encoding the FMDV empty capsid can modified in any suitable manner. Preferably, the nucleic acid sequence encoding the FMDV empty capsid is modified using methods known in the art for altering the tropism of viral coat proteins, such as adenoviral coat proteins (e.g., hexon protein).

When the empty capsid is used as a VLP, the empty capsid can deliver any suitable antigen to a mammalian host. For example, the antigen can be a tumor antigen. By "tumor antigen" is meant an antigen that is expressed by tumor cells but not normal cells, or an antigen that is expressed in normal cells but is overexpressed in tumor cells. Examples of suitable tumor antigens include, but are not limited to, β-catenin, BCR-ABL fusion protein, K-ras, N-ras, PTPRK, NY-ESO-1/LAGE-2, SSX-2, TRP2-INT2, CEA, gp100, kallikrein 4, prostate specific antigen (PSA), TRP-1/gp75, TRP-2, tyrosinase, EphA3, HER-2/neu, MUC1, p53, mdm-2, PSMA, RAGE-1, surviving, telomerase, and WT1. Other tumor antigens are known in the art and are described in, for example, The Peptide Database of T-Cell Defined Tumor Antigens, maintained by the Ludwig Institute for Cancer Research (www.cancerimmunity.org/statics/databases.htm), Van den Eynde et al., *Curr. Opin. Immunol.,* 9: 684-93 (1997), Houghton et al., *Curr. Opin. Immunol.,* 13: 134-140 (2001), and van der Bruggen et al., *Immunol. Rev.,* 188: 51-64 (2002).

Alternatively, the empty capsid can be used to deliver a bacterial antigen to a mammalian host. The bacterial antigen can originate from any bacterium including, but not limited to, *Actinomyces, Anabaena, Bacillus, Bacteroides, Bdellovibrio, Caulobacter, Chlamydia, Chlorobium, Chromatium, Clostridium, Cytophaga, Deinococcus, Escherichia, Halobacterium, Heliobacter, Hyphomicrobium, Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema.*

The empty capsid also can be used to deliver a parasite antigen to a mammalian host. The parasite antigen can originate from, for example, a parasite of the phylum Sporozoa (also referred to as phylum Apicomplexa), Ciliophora, Rhizopoda, or Zoomastigophora. Preferably, the antigen is a parasite of the phylum Sporozoa and genus *Plasmodium.* The antigen can be from any suitable *Plasmodium* species, but preferably is from a *Plasmodium* species that infects humans and causes malaria. Particularly preferred *Plasmodium* antigens include, for example, circumsporozoite protein (CSP), sporozoite surface protein 2 (SSP2), liver-stage antigen 1 (LSA-1), Pf exported protein 1 (PfExp-1)/Py hepatocyte erythrocyte protein 17 (PyHEP 17), Pf Antigen 2, merozoite surface protein 1 (MSP-1), merozoite surface protein 2 (MSP-2), erythrocyte binding antigen 175 (EBA-175), ring-infected erythrocyte surface antigen (RESA), serine repeat antigen (SERA), glycophorin binding protein (GBP-130), histidine rich protein 2 (HRP-2), rhoptry-associated proteins 1 and 2 (RAP-1 and RAP-2), erythrocyte membrane protein 1 (PfEMP1), and apical membrane antigen 1 (AMA-1).

In another embodiment of the invention, the adenoviral vector can comprise at least one nucleic acid sequence encoding a cytokine. "Cytokines" are known in the art as non-antibody proteins secreted by specific cells (e.g., inflammatory leukocytes and some non-leukocytic cells), that act as intercellular mediators, such as by regulating immunity, inflammation, and hematopoiesis. Cytokines generally act locally in a paracrine or autocrine rather than endocrine manner. Cytokines can be classified as a lymphokine (cytokines made by lymphocytes), a monokine (cytokines made by monocytes), a chemokine (cytokines with chemotactic activities), and an interleukin (cytokines made by one leukocyte and acting on other leukocytes). The cytokine can be any suitable cytokine known in the art, including, but not limited to, interferons, interleukins, RANTES, MCP-1, MIP-1$\alpha$, and MIP-1$\beta$, granulocyte monocyte colony-stimulating factor (GM-CSF), and tumor necrosis factor (TNF) alpha. In a preferred embodiment, the cytokine is an interferon. In this regard, the adenoviral vector can comprise at least one nucleic acid sequence encoding an interferon in addition to the at least one nucleic acid sequence encoding an *aphthovirus* antigen. Alternatively, the adenoviral vector comprises at lease one nucleic acid sequence encoding an interferon and lacks a nucleic acid sequence encoding an *aphthovirus* antigen. In either embodiment, the nucleic acid sequence can encode any suitable interferon (IFN). Suitable interferons include, for example, Type I and Type II interferons. Type I interferons include IFN-alpha, IFN-beta, IFN-delta, IFN-omega, and IFN-tau. Type II interferons include IFN-gamma. Interferons are a heterogeneous group of proteins with some similar biological activities that are distinguished from each other by many different physical and immunochemical properties. They are also encoded by different structural genes. The human interferons IFN-beta and IFN-gamma are encoded by two different single genes while human IFN-alpha constitutes a family of at least 23 different genes. Most interferons are multifunctional proteins with bioactivities that are strictly species-specific. IFNs are synthesized following the activation of the immune system. In particular, IFNs are mainly known for their antiviral activities against a wide spectrum of viruses. IFNs are synthesized, for example, by virus-infected cells and protect other, non-infected but virus-sensitive cells against infection. In addition, interferons are also known to have protective effects against some non-viral pathogens.

IFN-alpha and IFN-beta (IFN-alpha/beta) are known to have antiviral activity and are the first line of host cell defense against virus infection (see, e.g., Fields et al., eds., *Virology*, Lippincott-Raven Publishers, Philadelphia (1996)). Virus-infected cells are induced to express and secrete IFN alpha/beta, which binds to specific receptors on neighboring cells, priming them to a virus resistant state via a series of events leading to activation of IFN alpha/beta-stimulated genes (ISGs) (e.g., double-stranded (ds) RNA dependent protein kinase (PKR), 2'-5'A synthetase/RNase L and Mx). The products of these genes affect viruses at different stages of their replication cycle, and different viruses are susceptible to different ISG products. It has been demonstrated that FMDV replication is highly sensitive to IFN-alpha or -beta, and that supernatant fluids containing porcine or bovine IFN-alpha/beta inhibit FMDV replication (see Chinsangaram et al., *J. Virol.,* 73: 9891-9898 (1999)).

While in some embodiments of the invention the adenoviral vector preferably comprises one nucleic acid sequence encoding an *aphthovirus* antigen and/or one nucleic acid sequence encoding a cytokine, in other embodiments of the invention the adenoviral vector can comprise two or more (e.g., 2, 3, 4, 5, 6, 7, 8, 9, 10, or more) nucleic acid sequences, each of which encodes a different *aphthovirus* antigen, or a different cytokine. In this respect, each of the two or more nucleic acid sequences preferably encodes a different *aphthovirus* antigen, a different cytokine, or combinations thereof. For example, the adenoviral vector can comprise two or more nucleic acid sequences, in which (i) each nucleic acid sequence encodes a different *aphthovirus* antigen, (ii) each nucleic acid encodes a different cytokine, (iii) one *aphthovirus* antigen-encoding nucleic acid sequence and two or more cytokine-encoding nucleic acid sequences, or (iv) one cytokine-encoding nucleic acid sequence and two or more *aphthovirus* antigen-encoding nucleic acid sequences.

It will be appreciated that an entire, intact viral, bacterial, or parasitic protein is not required to produce an immune response. Indeed, most antigenic epitopes are relatively small in size, and, therefore, protein fragments can be sufficient for exposure to the immune system of the mammal. In addition, a fusion protein can be generated between two or more antigenic epitopes of one or more antigens. Delivery of fusion proteins via adenoviral vector to a mammal allows exposure of an immune system to multiple antigens and, accordingly, enables a single vaccine composition to provide immunity against multiple pathogens. In addition, the nucleic acid sequence encoding a particular antigen can be modified to enhance the recognition of the antigen by the mammalian host.

Each of the nucleic acid sequences in the inventive adenoviral vector is desirably present as part of an expression cassette, i.e., a particular nucleotide sequence that possesses functions which facilitate subcloning and recovery of a nucleic acid sequence (e.g., one or more restriction sites) or expression of a nucleic acid sequence (e.g., polyadenylation or splice sites). Each nucleic acid is preferably located in the E1 region (e.g., replaces the E1 region in whole or in part) and/or the E4 region of the adenoviral genome. For example, the E1 region can be replaced by one or more promoter-variable expression cassettes comprising a nucleic acid. Alternatively, in embodiments where the adenoviral vector contains the E1 region but is deficient in the E4 region, the E4 region can be replaced by one or more expression cassettes. In this manner, inserting an expression cassette into the E4 region of the adenoviral genome inhibits formation of "revertant E1 adenovectors" (REA), because homologous recombination within the E1 region and the E1 DNA of a complementing cell line (e.g., 293 cell) or helper virus results in an E1-containing adenoviral genome that is too large for packaging inside an adenovirus capsid. Each expression cassette can be inserted in a 3'-5' orientation, e.g., oriented such that the direction of transcription of the expression cassette is opposite that of the surrounding adjacent adenoviral genome. However, it is also appropriate for an expression cassette to be inserted in a 5'-3' orientation with respect to the direction of transcription of the surrounding genome. In this regard, it is possible for the inventive adenoviral vector to comprise at least one nucleic acid sequence that is inserted into, for example, the E1 region in a 3'-5' orientation, and at least one nucleic acid sequence inserted into the E4 region in a 5'-3' orientation. The E1 and/or the E4 region can be replaced by two or more expression cassettes (e.g., a dual expression cassette). In this embodiment, each of the expression cassettes can be positioned in any orientation with respect to each other. For example, two expression cassettes can be positioned such that each of the respective promoters is adjacent to the other. In this manner, one expression cassette is in a 5'-3' orientation with respect to the direction of transcription of the adenoviral genome and the other expression cassette is in a 3'-5' orientation. By positioning two promoters adjacent to each other, the activity of one of the promoters can be enhanced by the activity of the adjacent promoter.

In accordance with the invention, at least one nucleic acid sequence (e.g., one, two, three, or more nucleic acid sequences) is located in the E1 region of the adenoviral genome, and at least one nucleic acid sequence (e.g., one, two, three, or more nucleic acid sequences) is located in the E4 region of the adenoviral genome. While not preferred, all of the nucleic acid sequences can be located in either the E1 region or the E4 region of the adenoviral genome. In embodiments where the adenoviral vector comprises two or more nucleic acid sequences encoding an *aphthovirus* antigen and/or a cytokine, each of the two or more nucleic acid sequences preferably are located in the E1 region or the E4 region of the adenoviral genome. The insertion of an expression cassette into the adenoviral genome (e.g., into the E1 region of the genome) can be facilitated by known methods, for example, by the introduction of a unique restriction site at a given position of the adenoviral genome. As set forth above, preferably all or part of the E3 region of the adenoviral vector also is deleted.

Preferably, each nucleic acid sequence is operably linked to (i.e., under the transcriptional control of) one or more promoter and/or enhancer elements, for example, as part of a promoter-variable expression cassette. Techniques for operably linking sequences together are well known in the art. Any promoter or enhancer sequence can be used in the context of the invention, so long as sufficient expression of the nucleic acid sequence is achieved and a robust immune response is generated. Preferably, the promoter is a heterologous promoter, in that the promoter is not obtained from, derived from, or based upon a naturally occurring promoter of the adenoviral vector. In this regard, the promoter can be a viral promoter. Suitable viral promoters include, for example, cytomegalovirus (CMV) promoters, such as the mouse CMV immediate-early promoter (mCMV) or the human CMV immediate-early promoter (hCMV) (described in, for example, U.S. Pat. Nos. 5,168,062 and 5,385,839), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.,* 78: 144-145 (1981)), promoters derived from SV40 or Epstein Barr virus, an adenovirus promoter, such as the pIX promoter, an adeno-associated viral promoter, such as the p5 promoter, and the like.

Alternatively, the promoter can be a cellular promoter, i.e., a promoter that is native to eukaryotic, preferably animal, cells. In one aspect, the cellular promoter is a human cellular promoter or a bovine cellular promoter. In another aspect, the cellular promoter is preferably a constitutive promoter that works in a variety of cell types, such as cells associated with the immune system. Suitable constitutive promoters can drive expression of genes encoding transcription factors, housekeeping genes, or structural genes common to eukaryotic cells. Suitable cellular promoters include, for example, a ubiquitin promoter (e.g., a UbC promoter) (see, e.g., Marinovic et al., *J. Biol. Chem.,* 277(19): 16673-16681 (2002)), a human β-actin promoter, a chicken β-actin promoter, an EGR promoter, an EF-1α promoter, a YY1 promoter, a basic leucine zipper nuclear factor-1 (BLZF-1) promoter, a neuron specific enolase (NSE) promoter, a heat shock protein 70B (HSP70B) promoter, and a JEM-1 promoter.

Many of the above-described promoters are constitutive promoters. Instead of being a constitutive promoter, the promoter can be an inducible promoter, i.e., a promoter that is up- and/or down-regulated in response to an appropriate signal. The use of a regulatable promoter or expression control sequence is particularly applicable to DNA vaccine development inasmuch as antigenic proteins, including viral and parasite antigens, frequently are toxic to complementing cell lines. A promoter can be up-regulated by a radiant energy source or by a substance that distresses cells. For example, an expression control sequence can be up-regulated by drugs, hormones, ultrasound, light activated compounds, radiofrequency, chemotherapy, and cyofreezing. Thus, the promoter sequence that regulates expression of the nucleic acid sequence encoding the antigen and/or cytokine can contain at least one heterologous regulatory sequence responsive to regulation by an exogenous agent. In one embodiment, the regulatory sequences operably linked to the antigen-encoding and/or cytokine-encoding nucleic acid sequences include components of the tetracycline expression system, e.g., tet operator sites. For instance, the antigen-encoding nucleic acid sequence is operably linked to a promoter which is operably linked to one or more tet operator sites. When grown in complementing cells that express the tet repressor protein (tetR), the expression of the antigen-encoding or cytokine-encoding nucleic acid sequence is inhibited as a result of the tetR protein binding to the tetO sites. As a result, adenoviral vector production proceeds without the interference of large or potentially toxic transgenes. Other suitable inducible promoter systems include, but are not limited to, the IL-8 promoter, the metallothionine inducible promoter system, the bacterial lacZYA expression system, and the T7 polymerase system. Further, promoters that are selectively activated at different developmental stages (e.g., globin genes are differentially transcribed from globin-associated promoters in embryos and adults) can be employed.

The promoter can be a tissue-specific promoter, i.e., a promoter that is preferentially activated in a given tissue and results in expression of a gene product in the tissue where activated. A tissue-specific promoter suitable for use in the invention can be chosen by the ordinarily skilled artisan based upon the target tissue or cell-type. Preferred tissue-specific promoters for use in the inventive method are specific to immune cells, such as the dendritic-cell specific Dectin-2 promoter described in Morita et al., *Gene Ther.,* 8: 1729-37 (2001).

In yet another embodiment, the promoter can be a chimeric promoter. A promoter is "chimeric" in that it comprises at least two nucleic acid sequence portions obtained from, derived from, or based upon at least two different sources (e.g., two different regions of an organism's genome, two different organisms, or an organism combined with a synthetic sequence). Preferably, the two different nucleic acid sequence portions exhibit less than about 40%, more preferably less than about 25%, and even more preferably less than about 10% nucleic acid sequence identity to one another (which can be determined by methods described elsewhere herein). Chimeric promoters can be generated using standard molecular biology techniques, such as those described in Sambrook et al., supra, and Ausubel et al., supra.

A promoter can be selected for use in the invention by matching its particular pattern of activity with the desired pattern and level of expression of the antigen or cytokine. In embodiments where the adenoviral vector comprises two or more nucleic acid sequences encoding an antigen, the two or more antigen-encoding nucleic acid sequences are operably linked to different promoters displaying distinct expression profiles. For example, a first promoter is selected to mediate an initial peak of antigen production, thereby priming the immune system against an encoded antigen. A second promoter is selected to drive production of the same or different antigen such that expression peaks several days after the initial peak of antigen production driven by the first promoter, thereby "boosting" the immune system against the antigen. Alternatively, a chimeric promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. In addition, a promoter can be modified to include heterologous elements that enhance its activity. For example, a human CMV promoter sequence can include a synthetic splice signal, which enhances expression of a nucleic acid sequence operably linked thereto. In that antigens can be toxic to eukaryotic cells, it may be advantageous to modify the promoter to decrease activity in complementing cell lines used to propagate the adenoviral vector.

When the adenoviral vector comprises two or more nucleic acid sequences, the multiple nucleic acid sequences can be operably linked to the same or different promoters. In a preferred embodiment of the invention, each nucleic acid sequence is operably linked to a separate promoter. While it is preferred that each promoter is different, one or ordinary skill in the art will appreciate the advantages of using one particularly efficient promoter to control expression of each nucleic acid sequence present in the adenoviral vector. Thus, each nucleic acid sequence can be operably linked to the same promoter. In one aspect of the invention, the two or more nucleic acid sequences are operably linked to one or more different promoters (e.g., two nucleic acid sequences are each operably linked to the same promoter, or each nucleic acid sequence is operably linked to a different promoter). Most preferably, each of the two or more nucleic acid sequences is operably linked to a different promoter. The selection of an appropriate promoter for a given nucleic acid sequence will depend upon a number of factors, including promoter strength and the position of the expression cassette within the adenoviral genome, and can be performed using routine methods known in the art.

To optimize protein production, preferably the nucleic acid sequence further comprises a polyadenylation site 3' of the coding sequence. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the nucleic acid sequence is properly expressed in the cells into which it is introduced. If desired, the nucleic acid sequence also can incorporate splice sites (i.e., splice acceptor and splice donor sites) to facilitate mRNA production.

The invention further provides a method of inducing an immune response against an *aphthovirus* in a mammal, comprising administering to a mammal infected by an *aphthovirus* a composition comprising the aforementioned adenoviral vector and a pharmaceutically acceptable carrier, wherein the *aphthovirus* antigen and/or cytokine are expressed in the mammal to induce an immune response against the *aphthovirus*. Descriptions of the adenoviral vectors, *aphthovirus* antigen, and cytokine set forth above in connection with other embodiments of the invention also are applicable to those same aspects of the aforesaid method.

In the method of the invention, the adenoviral vector preferably is administered to a mammal, wherein the nucleic acid sequence(s) encoding the *aphthovirus* antigen and/or cytokine is (are) expressed to induce an immune response against the *aphthovirus*. The mammal can be any suitable mammal, but preferably is a cloven-hooved animal. Suitable cloven-hooved animals include, for example, sheep, cattle, swine, goats, and deer. The immune response can be a humoral immune response, a cell-mediated immune response, or, desirably, a combination of humoral and cell-mediated immunity. Ideally, the immune response provides protection upon subsequent challenge with the infectious agent comprising the antigen. However, protective immunity is not required in the context of the invention. The inventive method further can be used for antibody production and harvesting.

Administering the adenoviral vector encoding the antigen and/or cytokine can be one component of a multistep regimen for inducing an immune response in a mammal. In particular, the inventive method can represent one arm of a prime and boost immunization regimen. The inventive method, therefore, can comprise administering to the mammal a priming gene transfer vector comprising at least one nucleic acid sequence encoding an antigen and/or an cytokine prior to administering the adenoviral vector. The antigen and/or cytokine encoded by the priming gene transfer vector can be the same or different from the antigen and/or cytokine of the adenoviral vector. The inventive adenoviral vector is then administered to boost the immune response to a given pathogen. More than one boosting composition comprising the adenoviral vector can be provided in any suitable timeframe (e.g., at least about 1 week, 2 weeks, 4 weeks, 8 weeks, 12 weeks, 16 weeks, or more following priming) to maintain immunity.

Any gene transfer vector can be employed as a priming gene transfer vector, including, but not limited to, a plasmid, a retrovirus, an adeno-associated virus, a vaccinia virus, a herpesvirus, an alphavirus, or an adenovirus. Ideally, the priming gene transfer vector is a plasmid or an adenoviral vector. To maximize the effect of the priming regimen, the priming gene transfer vector can comprise more than one nucleic acid sequence encoding an antigen and/or a cytokine. Preferably, the priming gene transfer vector comprises two or more (e.g., 2, 3, 5, or more) nucleic acid sequences each encoding an antigen and/or a cytokine. Alternatively, an immune response can be primed or boosted by administration of the antigen itself, e.g., an antigenic protein, the cytokine itself, intact pathogen (e.g., *aphthovirus* particles), inactivated pathogen, and the like.

Any route of administration can be used to deliver the adenoviral vector to the mammal. Indeed, although more than one route can be used to administer the adenoviral vector, a particular route can provide a more immediate and more effective reaction than another route. Preferably, the adenoviral vector is administered via intramuscular injection. A dose of adenoviral vector also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The adenoviral vector can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir, an implant, or a device comprised of a polymeric composition, are particularly useful for administration of the adenoviral vector. The adenoviral vector also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of adenoviral vector administered to the mammal will depend on a number of factors, including the size of a target tissue, the extent of any side-effects, the particular route of administration, and the like. The dose ideally comprises an "effective amount" of adenoviral vector, i.e., a dose of adenoviral vector which provokes a desired immune response in the mammal. The desired immune response can entail production of antibodies, protection upon subsequent challenge, immune tolerance, immune cell activation, and the like. Desirably, a single dose of adenoviral vector comprises at least about $1\times10^5$ particles (which also is referred to as particle units) of the adenoviral vector. The dose preferably is at least about $1\times10^6$ particles (e.g., about $1\times10^6$-$1\times10^{12}$ particles), more preferably at least about $1\times10^7$ particles, more preferably at least about $1\times10^8$ particles (e.g., about $1\times10^8$-$1\times10^{11}$ particles), and most preferably at least about $1\times10^9$ particles (e.g., about $1\times10^9$-$1\times10^{10}$ particles) of the adenoviral vector. The dose desirably comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ particles). In other words, a single dose of adenoviral vector can comprise, for example, about $1\times10^6$ particle units (pu), $2\times10^6$ pu, $4\times10^6$ pu, $1\times10^7$ pu, $2\times10^7$ pu, $4\times10^7$ pu, $1\times10^8$ pu, $2\times10^8$ pu, $4\times10^8$ pu, $5\times10^8$ pu, $1\times10^9$ pu, $2\times10^9$ pu, $4\times10^9$ pu, $5\times10^9$ pu, $1\times10^{10}$ pu $2\times10^{10}$ pu, $4\times10^{10}$ pu, $1\times10^{11}$ pu, $2\times10^{11}$ pu, $4\times10^{11}$ pu, $1\times10^{12}$ pu, $2\times10^{12}$ pu, or $4\times10^{12}$ pu of the adenoviral vector.

The adenoviral vector desirably is administered in a composition, preferably a pharmaceutically acceptable (e.g., physiologically acceptable) composition, which comprises a carrier, preferably a pharmaceutically (e.g., physiologically acceptable) carrier and the adenoviral vector. Any suitable carrier can be used within the context of the invention, and such carriers are well known in the art. The choice of carrier will be determined, in part, by the particular site to which the composition is to be administered and the particular method used to administer the composition. Ideally, in the context of adenoviral vectors, the composition preferably is free of replication-competent adenovirus. The composition can optionally be sterile or sterile with the exception of the inventive adenoviral vector.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the adenoviral vector for use in the inventive method is administered in a composition formulated to protect the expression vector from damage prior to administration. For example, the composition can be formulated to reduce loss of the adenoviral vector on devices used to prepare, store, or administer the expression vector, such as glassware, syringes, or needles. The composition can be formulated to decrease the light sensitivity and/or temperature sensitivity of the expression vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for adenoviral vector-containing compositions are further described in, for example, U.S. Pat. No. 6,225,289, U.S. Pat. No. 6,514,943, U.S. Patent Application Publication 2003/0153065 A1, and International Patent Application Publication WO 00/34444. A composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the viral vector. As discussed herein, immune system stimulators or adjuvants, e.g., interleukins, lipopolysaccharide, and double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the invention but, of course, should not be construed as in any way limiting its scope.

EXAMPLE 1

This example demonstrates the production of an adenoviral vector comprising a nucleic acid sequence encoding an *aphthovirus* antigen.

An oligonucleotide containing two copies of the tet operator (5'-AGCTCTCCCTATCAGTGATAGAGATCTCCCTATCAGTGATAGAGATCGTCGACGA GCT-3') (SEQ ID NO: 4) was self-annealed, digested with SacI, and inserted at the SacI site between the TATA box and transcription start site of the CMV enhancer/promoter (GenBank X17403, nucleotides 174,314 to 173,566). An artificial untranslated sequence (UTR) of 144 base pairs and 3' splice site sequences were inserted downstream of the CMV sequences, followed by a nucleic acid sequence encoding the A24 Cruzeiro FMDV empty capsid and a simian virus-40 (SV40) polyadenylation signal. The resulting A24 empty capsid expression cassette was transferred to a shuttle plasmid containing adenovirus type 5 nucleotides 1-355 and 3333-5793 or 3511-5793 flanking the expression cassette and a restriction site for linearization.

Adenoviral vector genomes were constructed using the AdFast method (see U.S. Pat. No. 6,329,200). Briefly, *E. coli* strain BJDE3 was transfected with 100 ng of shuttle plasmid containing the A24 empty capsid expression cassette and 100 ng of a GV.11 base plasmid. The desired recombinant plasmids, containing deletions in the E1, E3, and E4 regions of the adenoviral genome and the expression cassette were identified by restriction digestion of DNA from individual bacterial colonies. The plasmids were further purified by transformation of recombination negative DH5α *E. coli* and single-colony isolation by standard microbiological methods. Isolation of a single genetic clone of the final vector genome was achieved by two sequential colony-growth steps in bacteria. The adenoviral vector plasmid structures were confirmed by restriction digestion analysis and DNA sequencing.

A 293-ORF6 cell line (Brough et al., *J. Virol.,* 70, 6497-6501 (1996)) stably expressing the TetR protein (293-ORF6TetR) was generated by transfecting 293-ORF6 cells with 2 μg of a HpaI-linearized pRSVTetR.hyg plasmid. After 24 hours the cells were split to ten 10 cm dishes and incubated in 250 μg/ml hygromycin.

293-ORF6TetR cells were transduced with the above-described E1-, E3-, E4-deleted adenoviral vectors comprising the nucleic acid sequence encoding the A24 FMDV empty capsid expressed under the control of a CMV-tetO promoter (A24 GV11).

Two research lots of the A24 GV11 vector were evaluated for the development of a serum antibody response against FMDV over time. One vector lot was produced and expanded in the 293-ORF6TetR cells, while the other was produced and expanded in 293-ORF6 cells. Cows were administered $5\times10^9$ pfu of each vector lot. At 4, 7, 14, and 21 days post inoculation, serum was obtained from treated cows, and anti-FMDV antibody responses were measured using methods known in the art. Both vector lots produced a significant anti-FMDV antibody titer.

The results of this example demonstrate that an E1/E4-deficient adenoviral vector comprising a nucleic acid sequence encoding an FMDV antigen elicits an antibody response in vivo.

EXAMPLE 2

This example demonstrates that an adenoviral vector encoding an FMDV antigen induces protection against FMDV challenge in cows.

A dose of $5\times10^8$ particle forming units (pfu) or $5\times10^9$ pfu of the A24 GV11 described in Example 1 was administered intramuscularly to cows (6 cows per dose) on "day 1". On day 7, cows were challenged with $2\times10^4$ infectious units directly injected into the tongue of vaccinated cows. Challenged cows were then evaluated for FMDV-induced lesions on their feet, as well as viremia.

In addition to challenge with direct inoculation of FMDV, a second group of six vaccinated cows were subject to contact challenge. Specifically, a dose of $5\times10^9$ pfu of the A24 GV11 vector described in Example 1 was administered intramuscularly to cows (6 cows per dose) on "day 1." Seven days post vaccination, cows were placed in contact (i.e., in the same room) with cows infected with FMDV.

Cows subject to direct inoculation challenge showed no systemic clinical disease, and no viremia occurred in all 12 vaccinated animals. Five of six vaccinated cows subject to contact challenge showed no systemic clinical disease. Only one of these six animals developed a tongue lesion. None of the contact-challenged cows developed viremia.

This example demonstrates a method of inducing a protective immune response against FMDV using the inventive adenoviral vector.

EXAMPLE 3

This example demonstrates that an adenoviral vector encoding an FMDV antigen induces protection against FMDV challenge in cows.

Figure 2B:
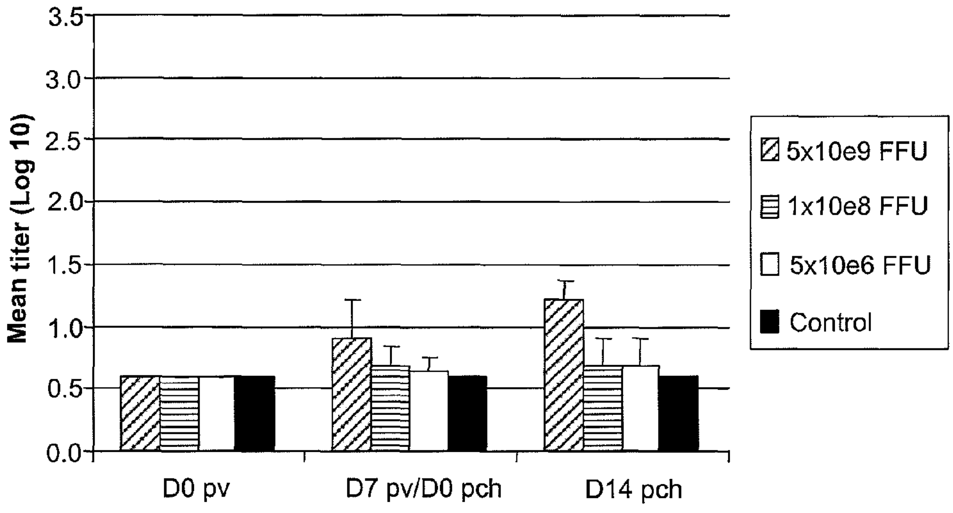
FIG. 2B is a graph illustrating the neutralizing antibody response against serotype 5 adenovirus in cattle produced as a result of the vaccination-challenge study described in Example 1. The antibody titers were measured prior to vaccination (D0pv), seven days after vaccination (D7 pv/D0 pch), and 14 days post challenge (D14 pch).

Four groups of 7 or 6 cows each were administered one of the following doses of the A24 GV11 adenoviral vector described in Example 1: Group A—$5\times10^9$ focus forming units (ffu), Group B—$1\times10^8$ ffu, Group C—$5\times10^6$ ffu, Group D—no adenovirus (control). Seven days after immunization, cows in each group were challenged with $1\times10^6$ infectious units of A24 FMDV directly injected into the tongue of vaccinated cows. Challenged cows were then evaluated for FMDV-induced fever, virus neutralizing antibody titer, virus isolation (positive or negative), and generalization of infection (e.g., presence, location, and number of lesions). The results of this experiment are set forth in FIGS. 1A-1D. Neutralizing antibody titers raised against FMDV serotype A24 and serotype 5 adenovirus also were measured in challenged cows using methods known in the art. The results of these experiments are set forth in FIGS. 2A and 2B.

Of the doses tested, the $5\times10^9$ ffu dose of A24 GV11 was most effective at inducing a protective immune response against FMDV challenge in cattle. In addition, vaccination with A24 GV11 elicited a neutralizing antibody response against the A24 FMDV, but did not elicit a significant neutralizing antibody response against the adenoviral vector backbone.

The results of this example demonstrate the effectiveness of a method of inducing a protective immune response against FMDV using the inventive adenoviral vector.

EXAMPLE 4

This example demonstrates that an adenoviral vector encoding an FMDV antigen induces protection against FMDV challenge in cows as well as an inactivated FMDV vaccine.

Five groups of cows each were administered a dose of the A24 GV11 adenoviral vector described in Example 1 or a dose of inactivated A24 FMDV according to the dosing schedule in Table 1.

TABLE 1

| Group | Number of Cows (n) | Vaccine | Dose | Day of Challenge post Vaccination | FMDV Challenge ($ID_{50}$) |
|---|---|---|---|---|---|
| A | 5 | A24 GV11 | $2\times10^9$ FFU | 7 | $1\times10^6$ |
| B | 5 | A24 GV11 | $2\times10^9$ FFU | 4 | $1\times10^6$ |
| C | 5 | Inactivated A24 | 2 mL | 7 | $1\times10^6$ |
| D | 5 | Inactivated A24 | 2 mL | 4 | $1\times10^6$ |
| E | 6 | None | N/A | N/A | $1\times10^6$ |

Figure 3A:
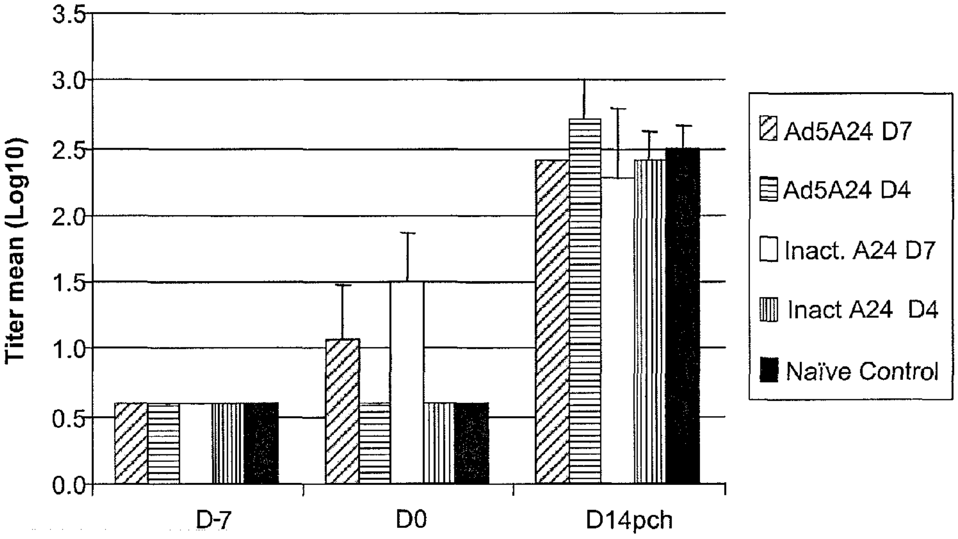
FIG. 3A is a graph illustrating the neutralizing antibody response against FMDV strain A24 in cattle produced as a result of the vaccination-challenge study described in Example 1. The antibody titers were measured seven days prior to vaccination (D7), the day of vaccination (D0), and 14 days post challenge (D14 pch).
Figure 3B:
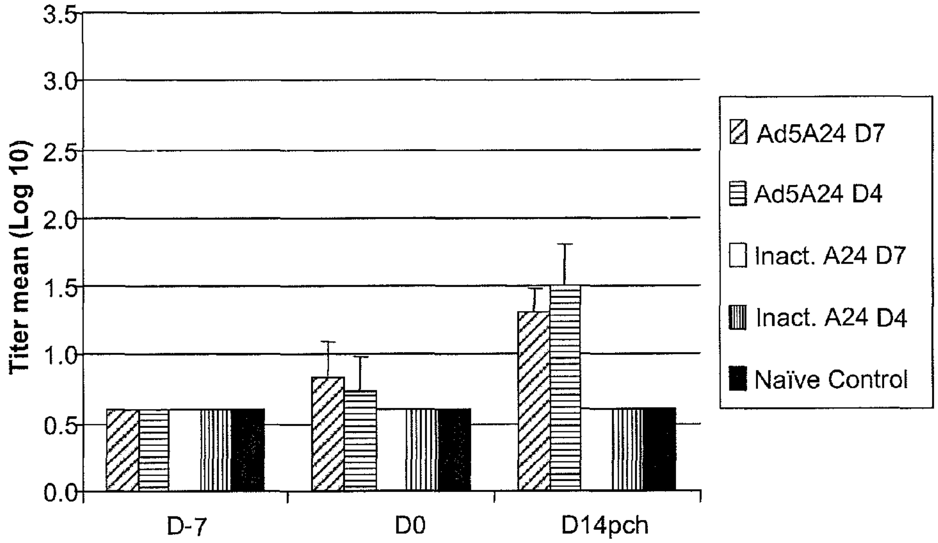
FIG. 3B is a graph illustrating the neutralizing antibody response against serotype 5 adenovirus in cattle produced as a result of the vaccination-challenge study described in Example 1. The antibody titers were measured seven days prior to vaccination (D7), the day of vaccination (D0), and 14 days post challenge (D14 pch).

At 4 days or 7 days after vaccination, vaccinated cows in each group were challenged with $1\times10^6$ infectious units of A24 FMDV directly injected into the tongue of vaccinated cows. Challenged cows were then evaluated for neutralizing antibody titers directed against A24 FMDV and serotype 5 adenovirus. The results of this study are set forth in FIGS. 3A and 3B.

Vaccination with A24 GV11 and inactivated A24 FMDV elicited similar neutralizing antibody responses against the A24 FMDV, but did not elicit a significant neutralizing antibody response against the adenoviral vector backbone. The results of this example demonstrate that the inventive adenoviral vector is as effective in generating an immune response against FMDV as is inactivated FMDV.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenoviral vector comprising an adenoviral genome and at least one nucleic acid sequence encoding an *Aphthovirus* empty virus capsid and optionally a cytokine operably linked to a promoter, wherein (i) the promoter consists of (a) SEQ ID NO:4, (b) a CMV enhancer/promoter sequence, (c) an untranslated region (UTR), and (d) one or more 3' splice sequences, and (ii) the adenoviral vector is replication-deficient and requires complementation of only the E1 region, only the E4 region, or only both the E1 and E4 regions of the adenoviral genome for propagation.

2. The adenoviral vector of claim 1, wherein the adenoviral vector comprises a first nucleic acid sequence encoding an *Aphthovirus* empty virus capsid and a second nucleic acid sequence encoding a cytokine, wherein the first and second nucleic acid sequences are different.

3. The adenoviral vector of claim 2, wherein the cytokine is an interferon.

4. The adenoviral vector of claim 3, wherein the interferon is selected from the group consisting of interferon alpha, interferon beta, and interferon gamma.

5. The adenoviral vector of claim 1, wherein the *Aphthovirus* is a foot-and-mouth disease virus (FMDV).

6. The adenoviral vector of claim 5, wherein the FMDV is of a serotype selected from the group consisting of A, 0, C, Asia 1, South African Territories (SAT) 1, SAT 2, and SAT 3.

7. The adenoviral vector of claim 5, wherein the FMDV is of strain A24 Cruzeiro.

8. The adenoviral vector of claim 1, wherein the adenoviral genome lacks the entire E1 region and at least a portion of the E4 region.

9. The adenoviral vector of claim 1, wherein the adenoviral genome lacks at least a portion of the E3 region.

* * * * *

UNITED STATES PATENT AND TRADEMARK OFFICE

CERTIFICATE OF CORRECTION

PATENT NO. : 8,323,663 B2
APPLICATION NO. : 12/117513
DATED : December 4, 2012
INVENTOR(S) : Brough et al.

It is certified that error appears in the above-identified patent and that said Letters Patent is hereby corrected as shown below:

Title Page, Item (63) Under Related U.S. Application Data, the year which reads, “2206,” should read, -- 2006 --

Signed and Sealed this
Twenty-first Day of May, 2013

Teresa Stanek Rea
*Acting Director of the United States Patent and Trademark Office*